United States Patent [19]
Fleischmann

[11] Patent Number: 5,814,067
[45] Date of Patent: Sep. 29, 1998

[54] SKIN PINCHING DEVICE

[76] Inventor: Wim Fleischmann, Nelkenweg 15, D-89182 Bernstadt, Germany

[21] Appl. No.: 860,006

[22] PCT Filed: Dec. 11, 1995

[86] PCT No.: PCT/DE95/01766

§ 371 Date: May 22, 1997

§ 102(e) Date: May 22, 1997

[87] PCT Pub. No.: WO96/18345

PCT Pub. Date: Jun. 20, 1996

[30] Foreign Application Priority Data

Dec. 12, 1994 [DE] Germany ............... 44 44 130.4

[51] Int. Cl.⁶ ................................................ A61B 17/08
[52] U.S. Cl. .................. 606/218; 606/54; 606/57; 606/59; 606/216; 606/217; 606/218; 606/205; 606/206
[58] Field of Search ................ 606/54, 57, 59, 606/214, 215, 216, 217, 218, 198, 151, 150, 205, 206, 207, 208

[56] References Cited

U.S. PATENT DOCUMENTS 2,450,194 9/1948 Glaser ........................... 128/20
5,263,971 11/1993 Hirschowitz et al. .

FOREIGN PATENT DOCUMENTS 0 269 935 6/1988 European Pat. Off. .
1412751 7/1988 Russian Federation .

*Primary Examiner*—Michael Buiz
*Assistant Examiner*—Daphna Shai
*Attorney, Agent, or Firm*—Stephan A. Pendorf, P.A.

[57] ABSTRACT

A skin pinching device has two jaws (10) that may be moved against each other by threaded spindle (36). Hooks (18) that may be stuck into the skin are arranged on the jaws (10, 12). The hooks (18) are cast into plastic parts (14) mounted on the jaws (10, 12) in an exchangeable manner. The threaded spindle (36) may be motor-driven in a controlled manner depending on the characteristics of the tissues as determined by a sensor.

13 Claims, 4 Drawing Sheets

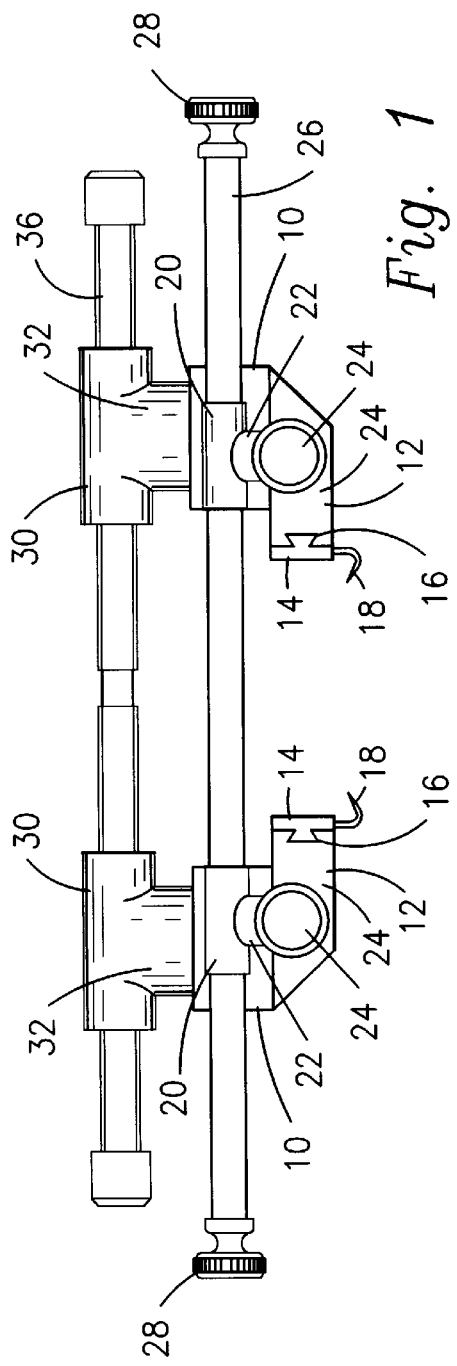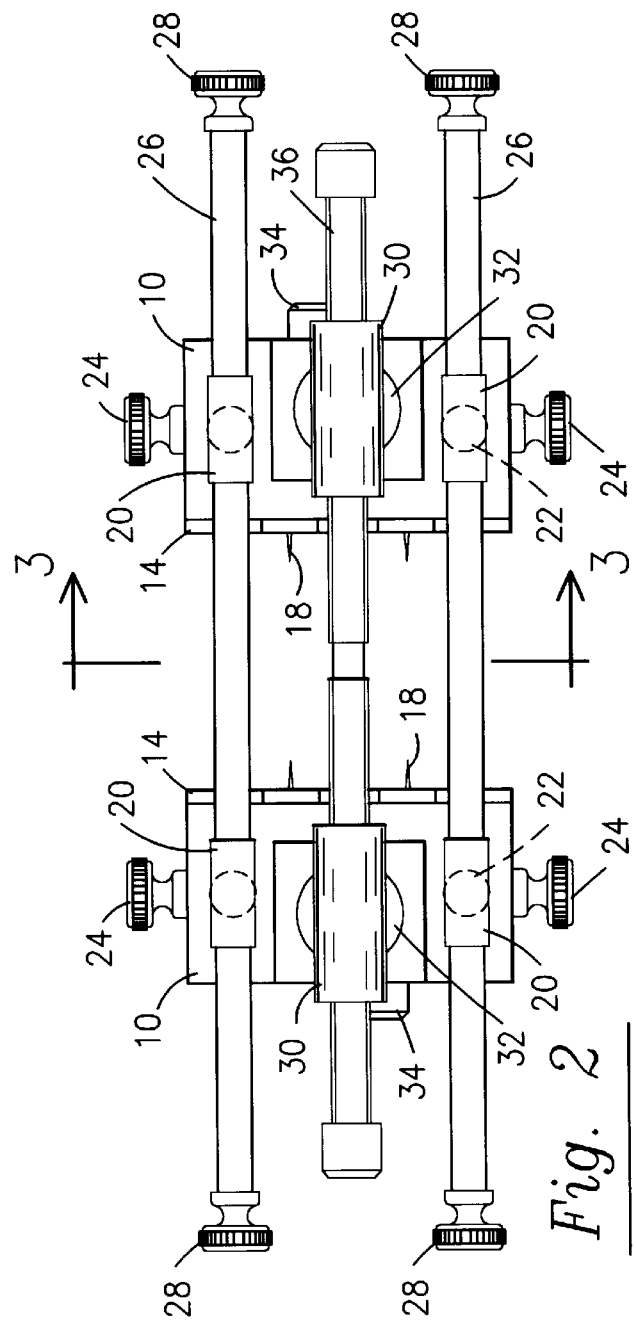

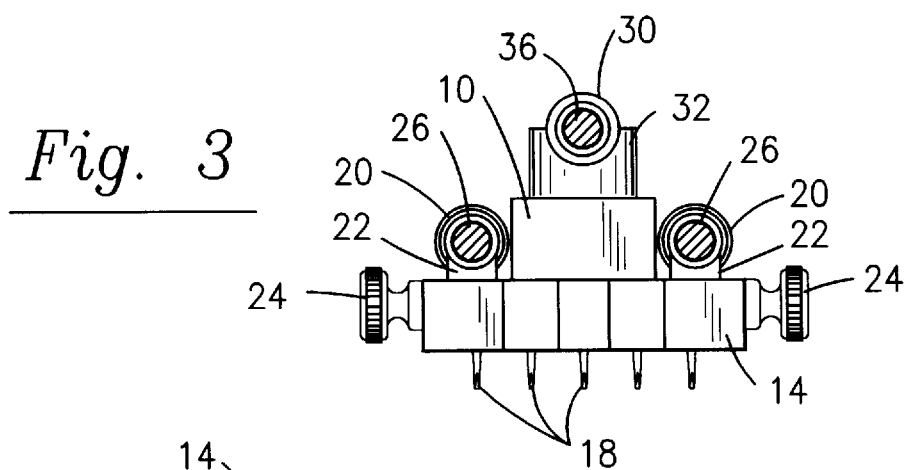
Fig. 3
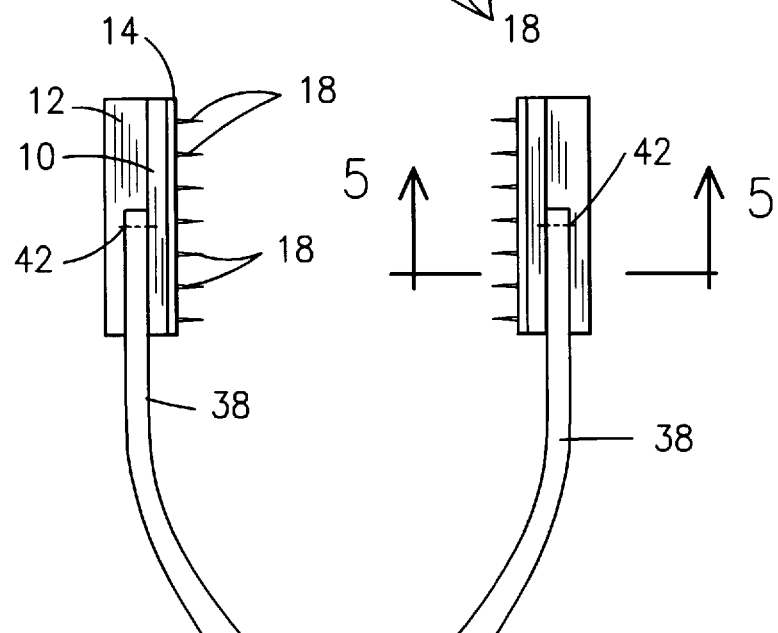
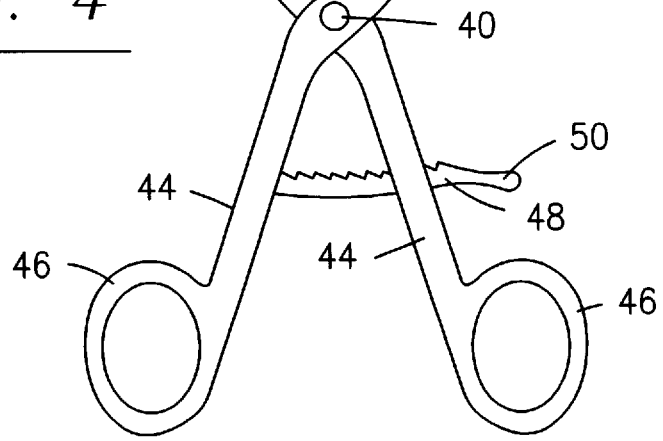
Fig. 4

SKIN PINCHING DEVICE

BACKGROUND OF THE INVENTION

1. Field of the Invention

The invention concerns a skin pinching device.

2. Description of the Related Art

Skin pinching devices of this type are used to draw together the skin along the wound edges of a large surface area wound. The drawing together of the edges of the wound can be accomplished within a short time of approximately 15 to 30 minutes, in order that the wound may be sutured (U.S. Pat. No. 4,896,680). Herein the skin is stretched in the area of the edges of the wound by taking advantage of the visco-elastic properties thereof. If however the wound edges are drawn together over a period of several days or weeks, then the wound can be closed with formation of new tissue, without requiring that the skin be stretched to is visco-elastic point.

From U.S. Pat. No. 5,263,971 a skin pinching device of the type discussed above is known. This skin pinching device includes two jaws with respectively two hooks each, which are inserted into the skin and are anchored in the skin via a transverse needle which can be stuck into the skin. The jaws are respectively seated upon a transverse track or rail. The transverse rails run parallel to each other and are capable of being adjusted with respect to their parallel spacing, so that the jaws can be moved toward each other, in order that the edges of the wound, in which the jaws are anchored via the hooks, are drawn together. For the parallel displacement of the transverse rails these are on the one hand slidingly guided upon a guide rail and are engaged on the other hand by a threaded spindle which runs parallel to the guide rail, by means of which an adjustment movement can be effectuated.

In this known skin pinching device the jaws are rigidly set to run at right angles with respect to the direction of adjustment. The needles which anchor the hooks in the skin must thus be inserted or seated exactly perpendicularly to the direction of contraction or displacement of the skin, in order to avoid uneven drawing tensions on the skin. An adaptation of the jaws and their anchoring in the skin to the contour of the wound edges is not possible. Besides this, the skin pinching device is a complex and expensive instrument, which is difficult to cleanse and sterilize.

SUMMARY OF THE INVENTION

The invention is concerned with the objective, of overcoming these disadvantages and of providing a skin pinching device which is more advantageous in its method of employment.

In the skin pinching device according to the invention, the hooks, which serve to anchor the jaws in the skin, are provided on a part, which is releasably and removably associated with the jaw. The hooks, which are stuck into the skin of the patient and which require a high degree of sterility, can in this manner be provided as single-use parts, which are respectively disposed of after use. The remaining complex and expensive skin pinching device can be cleansed, disinfected and reused repeatedly. Preferably the hooks are anchored in an injection mounded plastic part, so that the single use parts are produced in an exceptionally economical manner. The changing out and disposal of the parts with the hooks after use has the further advantage, that the danger of an injury and infection to the personnel during cleaning, disinfecting and storage of the skin pinching device due to the extremely sharp and pointed hooks is precluded.

The provision of the hooks in separate parts associated with the jaws of the skin pinching device has the further advantage, that the hooks can be stuck into the skin of the patient separately from the skin pinching device. The difficulty of sticking the hooks into the skin because of the pliability of the soft skin is thereby substantially overcome. After the sticking in of the hooks the parts with the hooks are secured to the jaws. The securing can be accomplished, for example, by means of a dove tail joint. Other securing possibilities are obvious to the person working in this art.

The plastic part with the hooks can be a strip or bar which extends along the entire breadth of the jaws, wherein the hooks are imbedded in a row side-by-side. Thereby the securing on the jaws and the change-out is simplified. It is also advantageous to have only a single hook, two hooks or a small number of hooks anchored in a single plastic part. Thereby the sticking in of the hooks into the skin is substantially simplified, since one or two hooks can in any case always be stuck into the skin next to each other without any problem. After the sticking in the hook-containing individual parts are modularly secured to the jaw one beside the other, for example, by sliding into a dove tail joint, in order that a row of hooks is thereby formed. In this manner also a large number of hooks can be provided in a jaw in a row without any problem, without any difficulty due to the sticking in of the hooks along the rim of the wound. The distance between the hooks in the row is determined by the breadth of the individual parts each respectively carrying a hook.

In accordance with the invention the jaws can be guided via guide boxes along two guide rails running in parallel in the direction of skin adjustment, wherein the guide boxes are mounted in the jaws to be rotatable about a vertical axis which is perpendicular to the plane of the adjustment movement. The guide rails can thereby be guided along the guide boxes, wherein the adjustment means for adjusting the spacing is separately provided. It is also possible that one or two of the guide rails can be constructed as threaded spindles, wherein the associated guide boxes are constructed as threaded bushings or screw sockets. The threaded spindle guide rails serve simultaneously as adjustment means and as spacer adjuster.

Further in accordance with the skin pinching device according to the invention, the two jaws can be provided on two arms, which are connected so as to swivel with respect to each other in the plane the adjustment direction. Thereby the results a particularly simple construction of the skin pinching device, which reduces the manufacturing costs and the simplifies operation.

This embodiment is particularly simple when the jaws are secured non-rotationally on the arms with respect to the plane of adjustment of the arms. Although the respective adjustments of the jaws occurs over an arched path, this is, however, not significant when the adjustment path, that is, the breadth of the wound, is not large and the length of the arms, that is, the radius of the arch, is not too small.

In order to make possible a tissue forming during the stretching of the skin, the jaws of the skin pinching devices are moved towards each other only slowly and in small steps and with large time intervals. For this a probe can be employed in accordance with the invention, which detects the condition of the skin in the area to be stretch on the side of the jaws opposite the side facing the wound. This can be, for example, a probe which determines the skin perfusion or the oxygen partial pressure. The adjustment means for adjusting the space between the jaws is operated in response to the values transmitted by the probe. Thereby on the one hand it is prevented that the skin is stretched too strongly and thereby damaged, and on the other hand the repositioning of the jaw separation can be accomplished at the earliest possible point in time, so that an optimal tissue growth and thereby a short as possible healing time is achieved.

If the adjustment means is driven by a motor, then an automatic readjustment corresponding to the values determined by the probe is possible.

BRIEF DESCRIPTION OF THE DRAWINGS

In the following the invention will be described in greater detail by reference to the embodiment shown in the drawings. There is shown:

FIG. 1 a side view of a skin pinching device,

FIG. 2 a top view of the skin pinching device of FIG. 1,

FIG. 3 a view according to section lines III—III in FIG. 2,

FIG. 4 a top view of a second embodiment of the skin pinching device,

DETAILED DESCRIPTION OF THE INVENTION

Figure 5:
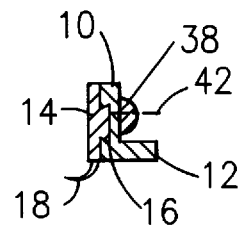
FIG. 5 a section according to lines V—V in FIG. 4.

In FIGS. 1 through 3 a first embodiment of the skin pinching device is shown.

The skin pinching device is comprised of two jaws 10 constructed with mirror image symmetry. The jaws 10 are designed so that their lower side takes the shape of a ski or runner, with which they rest upon the skin of the patient. On face side of the runners 12 which face each other a bar or strip 14 is provided, which extends along the entire breadth of the jaw 10. This bar 14 is secured to the face side of the runner 12 via a dove tail joint 16. To achieve this the bar 14 can be slid or pushed from the side into the dove tail guide 16 of the runner 12. The bar 14 is comprised of a plastic or synthetic material. Preferably a catch is provided, which retains the bar 14 in the inserted position. For this the bar 14 can have for example a small raised area, which elastically engages in a recess in the face side of the runner 12.

Hooks 18 of metal are encased in the bar 14. A plurality of hooks 18 are seated in a row next to each other in equal separation along the entire breadth of the bar 14. The hooks 18 extend from the lower small edge of the bar 14 downwards beyond the lower surface of the runner 12 and have their sharp tips bent away from the face side of the bar 14, so that the tips of the hooks 18 of the two jaws 10 are directed towards each other. The sharp tips of the hooks 18 are stuck into the cutis in the area of the rim of the wound and anchor the jaws 10 in the wound edges.

Instead of one bar 14 which extends along the entire breadth of the jaw 10, this can be divided in a modular manner into individual parts, which respectively exhibit only one hook 18 or very few hooks 18, as shown particularly in FIG. 3. The hooks 18 can thus individually be stuck into the edges of the wound, and the parts are sequentially introduced into the dove tail joint 16.

On the two narrow sides of the jaws 10 there are provided on the upper sides respectively guide boxes 20, of which the axis extends horizontally, that is, parallel to the lower glide surface of the runners 12. The guide boxes 20 are provided with journal pins 22 which extend perpendicular to their axis, which is perpendicular to the plane of the glide surface of the runners 12, and are seated from above rotatably in a borehole of the jaw 10. The guide boxes 20 are thus mounted rotatably about the axis of the journal pin 22, that is, mounted on the jaw 10 rotatabe about an axis perpendicular to the glide surface of the runner 12. The knurled headed screws 24 which are introduced into the side surfaces of the jaws 10 engage in a recess in the journal pins 22, in order to maintain or secure these axially in the jaw 10 and, as necessary, to secure them in their respective rotated positions.

The two jaws with their respective guide boxes 20 are seated respectively upon guide rails 26. The two jaws 10 are slidingly guided on the guide rails 26 by the guide boxes 20 and displaceable towards or away from each other, wherein the rotatable mounting of the guide boxes 20 in the jaw 10 makes it possible, that the jaws 10 can assume even a 90° offset angle with respect to the guide rails 26. The bars 14 with the hooks 18 of the two jaws 10 can in this manner not only be oriented parallel to each other, but rather also can assume an angle to each other. This makes possible the adaptation of the orientation of the hooks 18 to the respective contour of the wound edge.

The heads 28 of the screws introduced coaxially into the ends of the guide rails 26 make it possible to introduce the guide rails 26 into the guide boxes 20 and also to retain these on the guide rails 26 so that they cannot be lost.

Centrally upon the upper side of the jaws 10 there is respectively provided a threaded bushing 30, of which the axis is likewise horizontal, that is, extending parallel to the glide surface of the runner 12. The guide bushings 30 are seated on the upper side of the jaw 10 in mounting receptacles with journal pins 32 oriented at right angles to their axis, that is, oriented perpendicular to the glide surface of the runners 12. The threaded bushings 30 are thus mounted in the jaws 10 in a like manner to the guide boxes 20 pivotal about a vertical axis perpendicular to the plane of the glide surface of the runner 12. A screw 34 introduced into the back side of the jaw 10 engages in a recess in the journal pin 32, in order to retain this in the jaw 10 so it will not get lost. A common threaded spindle 36 passes through the threaded bushings 30 of the two jaws 10, which runs parallel to the guide rails 26. The threaded spindle 36 is centrally divided into two counter-rotating threaded sections, so that the threaded bushing 30 of one jaw 10 with the threaded spindle 36 forms a right-handed threading while the threaded bushing 32 on the other jaw 10 together with the threaded spindle 36 forms a left-handed threading. Upon a rotation of the threaded spindle 36 the two jaws 10 move therewith towards each other or away from each other.

In the use of the skin tensioning device, first the journal pins 22 of the guide boxes 20 are released so that the guide boxes 20 and the threaded bushings 30 can rotate or pivot about their respective journal pins 22 or, as the case may be, 32. The jaws 10 are anchored about the edges of the wound by their hooks 18, whereby the rotatability of the journal pin 22 and 32 makes possible an orientation of the jaws 10 in adaptation to the contour of the wound edge. As soon as the jaw with its hooks 18 is in place and anchored, the journal pins 22 are screwed or clamped tight via their knurl headed screws 24 so that the jaws 10 are secured in their respective angular positions with respect to the guide rails 26. Now the jaws 10 can be slid on the guide rails 26 towards each other by means of the threaded spindle 36 in order to draw together the edges of the wound, whereby the jaws 10 and their hooks 18 maintain the relationship to the contour of the wound edge.

After the closure of the wound edges the skin tensioning device is removed. The bars 14 with the hooks 18 are removed from the jaws 10 and disposed of. The balance of the skin pinching device is cleansed and sterilized. Only when ready for a new use, new bar 14 with hooks 18 is introduced into the jaws 10.

In FIGS. 4 and 5 a further embodiment of the skin pinching device is represented.

In correspondence with the first embodiment a bar 14 with hooks 18 is introduced into a dove tail 16 provided on a jaw 10 provided with a runner 12. For this, reference may be made to the above description.

Each of the jaws 10 is provided on the free end of an arm 38. The two arms 38 are pivotably connected with each other via a joint 40, so that the jaws 10 are pivotable towards each other along the plane of the glide surface of the runner 12.

The arms 38 are connected to the jaws 10 respectively by means of a pivotal joint 42 such that the jaws 10 are pivotal about an axis running in the direction of movement of the jaws 10. In the embodiment shown in FIG. 4 the arms 38 extend through the joint 40 and further out to a scissors grip 44 with finger holes 46. The scissors grip 44 is provided with a ratchet or détente mechanism, for which one of the branches of the scissors grip 44 is provided with a toothed rod, which engages with spring tension into a détente on the other branch and which can be lifted out of engagement from the détente via grip 50.

The skin pinching device in this embodiment is applied to the wound edges in the orientation shown in FIG. 4, and for this the bars 14 with their hooks 18 are anchored in the skin. By means of the scissors grip 44 the jaws 10 are moved toward each other, in order that the wound edges are drawn together. The drawing together can occur stepwise in accordance with the steps of the toothed rod 48. The arresting or détente of the toothed rod 48 detains the arms 38 with the jaws 10 against the tension of the skin.

When the wound edges are sufficiently drawn together and contact each other, the wound edges can be sutured each other. For this the scissors grips 44 with the arms 38 can as necessary be pivoted upwards out of the plane parallel to the glide surface of the runners 12 as shown in FIG. 4 and take a position, in which the arms 38 and the scissors grips 44 are perpendicular to the glide surface of the runners 12. The scissors grip 44, with the arms 38 when in this position, is no longer in the way, so that the wound edges on both sides of the jaw 10 are accessible and can be sutured from both sides up to the jaws 10.

Figure 6:
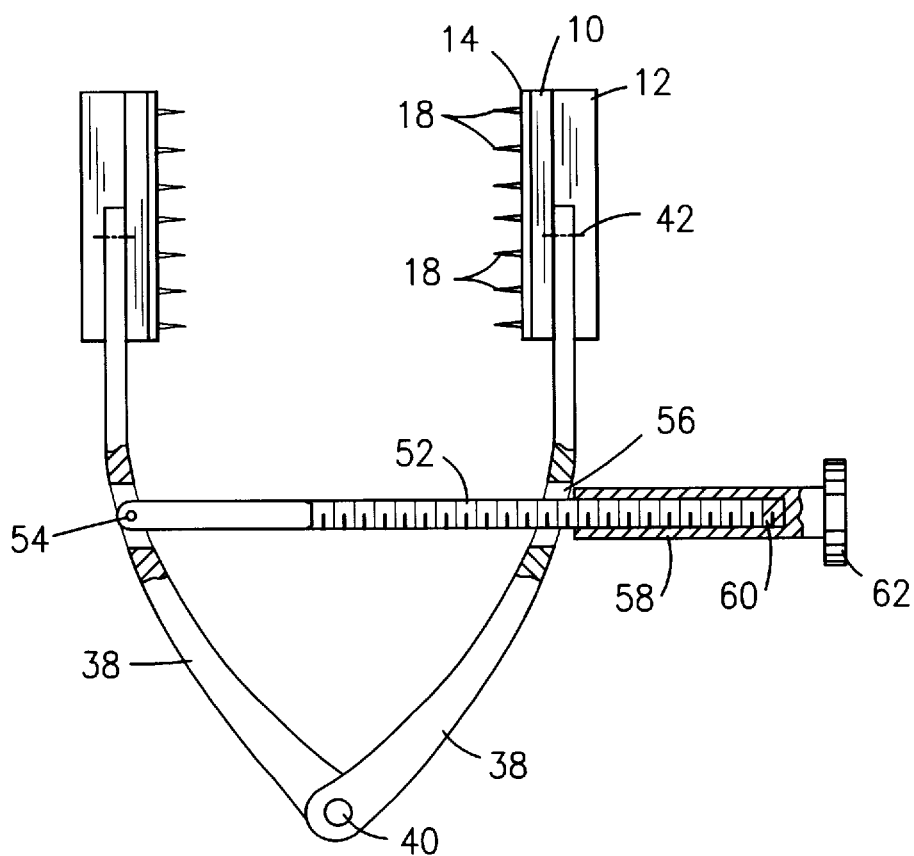
FIG. 6 a top view of a further embodiment of the skin pinching device.

In FIG. 6 a further embodiment of the skin pinching device is shown. This corresponds in substantial part with the embodiment according to FIG. 4, and for common elements reference may be made to the description of FIGS. 4 and 5.

In contrast to the exemplary embodiment of FIG. 4, in the exemplary embodiment according to FIG. 6 the adjusting means for adjusting the separation of the jaws 10 engages directly in the arms 38. For this a threaded rod 52 is pivotably mounted on the one arm 38 with one of its ends in a pivot point 54. The threaded rod 52 is thereby pivotable in the plane of the pivot movement of the arm 38. The threaded rod 52 transits freely through a through hole in the other arm 38 so that the threaded rod 52 does not prevent a relative pivoting between the arms 38. On the free end of the threaded rod 52 passing through the through hole 56 a positioning bolt 58 with a coaxial threaded bore 60 is screwed on. The end of the positioning bolt 58 screwed onto the threaded rod 52 abuts against the outside of arm 38. The positioning bolt 58 can be turned via a knurled knob 62 and therewith be moved along the threaded rod 52.

The skin pinching device according to FIG. 6 is applied to the wound in a manner similar to that already described with respect to FIG. 4. By turning of the positioning bolt 58 the arms 38 are pivoted towards each other and jaws 10 anchored on the wound edges are moved towards each other. The positioning bolt 58 supports at this time the arms 38 against the tension of the skin at the wound edges.

If the wound is to be closed by new tissue formation on the wound edges by means of the skin pinching device, then the jaws of the skin pinching device may only be moved towards each other in such steps and at such time intervals, that the tissue new formation can follow this movement of the wound edges. The adjustment or repositioning of the jaws can occur manually by adjustment of the threading (in the illustrative embodiments according to FIGS. 1–3 and FIG. 6) or as the case may be by closure of the scissors grip (in illustrative embodiment according to FIG. 4) according to empirical values. In order that the process is made more reliable and less dependent upon experience, the tissue new formation may be monitored by means of a suitable sensor. Such a sensor can monitor for example the perfusion of the tissue or the oxygen supply or as the case may be oxygen partial pressure in the tissue in the area which is placed under tension by the skin pinching device. The repositioning of the jaws occurs in such steps, that the characteristic values for over-stretching of the skin are not exceeded.

Here the repositioning of the skin pinching device can also occur manually according to the values determined by the sensor.

The monitoring of the skin pinching makes possible also an automatic repositioning of the skin pinching device, insofar as a motorized drive of the skin pinching device is provided. For such motor driven embodiments particularly the embodiments of the threaded adjusting means, for example according to FIGS. 1 through 3 and FIG. 6, are particularly suitable.

Figure 7:
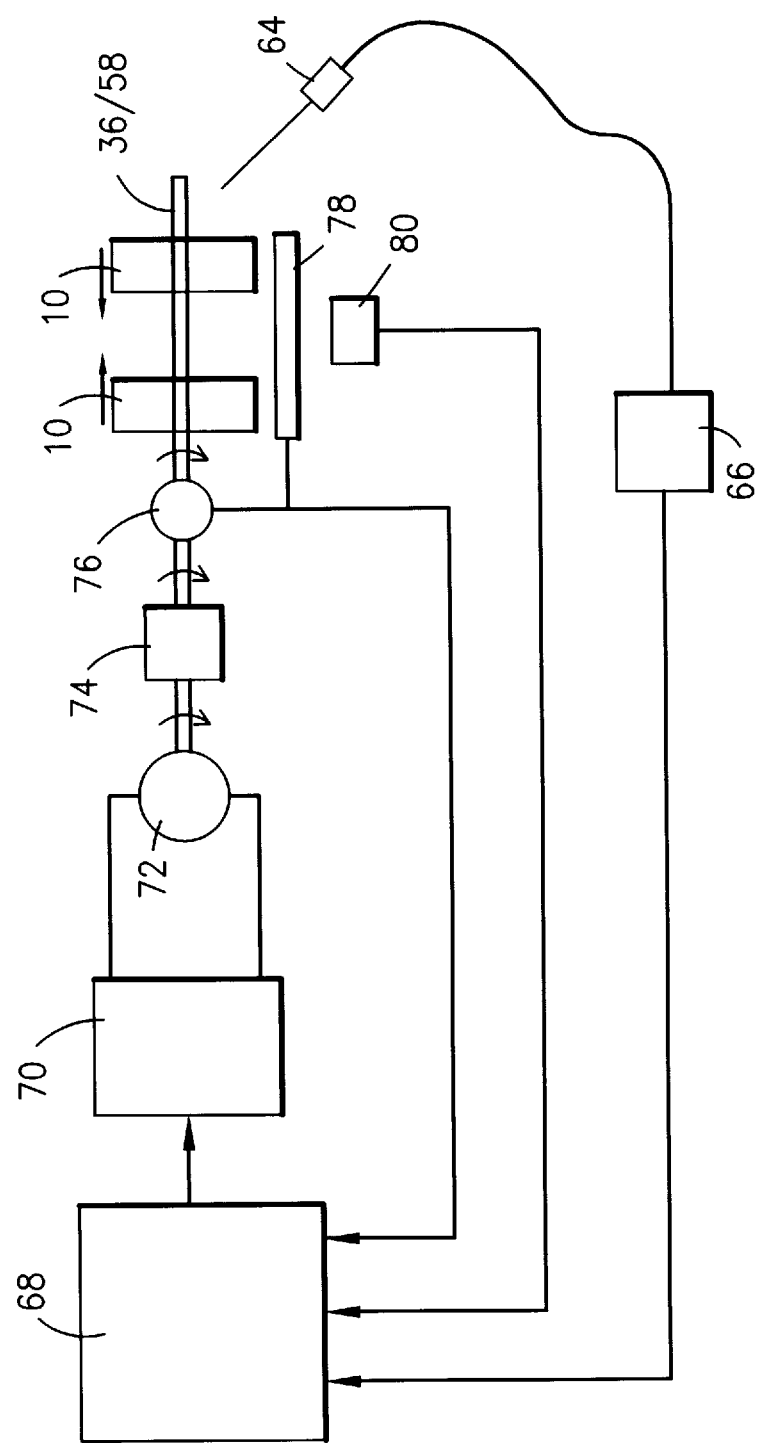
FIG. 7 a schematic representation of a control mechanism for the automatic repositioning of the skin pinching device.

In FIG. 7 a set-up for automatic repositioning of the skin pinching device for such an embodiment is schematically represented.

The jaws 10 of the skin pinching device are adjusted using threaded adjusting means, for example a threaded spindle 36 according to the embodiments shown in FIGS. 1 through 3 or an adjusting bolt 58 according to the embodiment of FIG. 6. A sensor 64 measures the condition of the skin tissue in the stretched area, that is, on the side of the jaw 10 opposite the side facing the wound. The sensor 64 measures for example the oxygen partial pressure in the tissue or the perfusion of the tissue using optical means. The measured values of the sensor 64 are converted into digital values in a measured value transformer 66, which are then further transmitted to a computer 68. The computer 68 controls, via a controller 70, a motor 72 which operates, via drive means 74, the threaded adjusting means 36/58 of the skin pinching device. The feedback back to the computer 68 as to the adjustment of the jaw 10 is accomplished by an encoder 76 coupled to the threaded adjustment means or by a path length measuring system 78 determining the separation between the jaws 10. In certain cases a tension measuring device 80 can also be provided in addition to or in place of the measuring of the tissue characteristics by means of the sensor 64, which measures the contraction forces which the jaws 10 are imparting upon the drawn skin and transmit this to the computer 68 as an actual value.

What is claimed is:

1. A skin pinching device comprising:

at least a pair of jaws, adjustment means for adjusting the spatial separation of the jaws with respect to each other, and two or more removable modules provided on each of said jaws, said modules capable of being sequentially assembled modularly on said laws so as to engage a guide channel (16) running in each jaw perpendicularly to the direction of adjustment, each of said modules including one or more hooks designed for sticking into skin, each jaw thereby forming a row of hooks.

2. A skin pinching device according to claim 1, wherein the number of hooks on at least one module is one.

3. A skin pinching device according to claim 1, wherein the number of hooks on at least one module is two.

4. A skin pinching device according to claim 1, wherein the number of hooks on at least one module is between one and seven.

5. A skin pinching device according to claim 1, wherein the total number of hooks on one jaw is five.

6. A skin pinching device according to claim 1, wherein said guide channel is a dove tail groove.

7. Skin pinching device according to claim 1, wherein said modules are comprised of plastic with hooks partially encased in said plastic.

8. Skin pinching device according to claim 1, wherein the number of hooks on at least one module is three.

9. Skin pinching device according to claim 1, wherein the number of hooks on at least one module is four.

10. Skin pinching device according to claim 1, wherein the number of hooks on at least one module is five.

11. Skin pinching device according to claim 1, wherein the number of hooks on at least one module is six.

12. Skin pinching device according to claim 1, wherein the number of hooks on at least one module is seven.

13. Skin pinching device according to claim 1, wherein the number of removable modules provided on each jaw is greater than two.

* * * * *